United States Patent [19]
Heim et al.

[11] Patent Number: 5,538,006
[45] Date of Patent: Jul. 23, 1996

[54] CONFIGURATION METHOD FOR AN ANESTHESIA PROTOCOL SYSTEM

[75] Inventors: Werner Heim, Herrenberg; Joachim Koeninger, Eutingen; Thomas Kerker, Kirchheim, all of Germany

[73] Assignee: Hewlett-Packard Company, Palo Alto, Calif.

[21] Appl. No.: 217,316

[22] Filed: Mar. 24, 1994

[30] Foreign Application Priority Data

Nov. 16, 1993 [DE] Germany ............... 43 39 155.9

[51] Int. Cl.$^6$ .................................................. G06F 159/00
[52] U.S. Cl. ........................................... 128/709; 128/710
[58] Field of Search ........................ 364/413.01, 900; 340/724, 703, 726, 521; 128/709, 710, 204.21, 204.23

[56] References Cited

U.S. PATENT DOCUMENTS

| | | | |
|---|---|---|---|
| 4,051,522 | 9/1977 | Healy et al. | 358/86 |
| 4,315,309 | 2/1982 | Colii | 364/200 |
| 4,356,475 | 10/1982 | Neuman et al. | 340/521 |
| 4,460,975 | 7/1984 | Torkelsen et al. | 364/900 |
| 4,974,386 | 12/1988 | Bedrij et al. | 340/724 |
| 5,270,530 | 12/1993 | Godleweski et al. | 250/208.1 |

FOREIGN PATENT DOCUMENTS

0457000A2  11/1991  European Pat. Off. .

*Primary Examiner*—Gail O. Hayes
*Assistant Examiner*—Frantzy Poinvil

[57] ABSTRACT

Vital parameters of patient and medication parameters are automatically combined to form anesthetic protocols. A multi-step configuration method facilitates anesthesia protocol system reconfiguration. All the groups which may be taken into account for a possible future reproduction of the anesthesia protocol are first defined by combining parameters to form a group. A configuration name is assigned to each group. In a subsequent step, each anesthesia protocol segment has one of the groups assigned to it. The steps of forming the groups and assigning the groups to segments are repeated for each configuration. In a subsequent on-line mode of the anesthesia protocol system, the operator reconfigures the system by using the configuration name.

7 Claims, 4 Drawing Sheets

CONFIGURATION METHOD FOR AN ANESTHESIA PROTOCOL SYSTEM

FIELD OF THE INVENTION

The present invention refers to an anethesia protocol system configuration method for the screen display of an anesthesia protocol and/or for the form of a printout of an anesthesia protocol, said screen display as well as said form of printout being determinable by an operator. When such a method is carried out, a plurality of parameters comprising vital parameters of the patient and/or a medication parameter and/or a parameter for an adjustment of gas and/or a machine parameter are generally combined in a manner which can be defined by the operator for obtaining the screen display and/or the printout of the anesthesia protocol.

DESCRIPTION OF THE PRIOR ART

In all hospitals it has been common practice for decades that anesthesia protocols are manually recorded by the anesthetist in the course of each anesthesia carried out.

A typical anesthesia protocol includes two areas above the time axis, viz. an upper area indicative of the variation with time of the medication, i.e. the administration of medicaments e.g. in absolute amounts or, in the case of anesthetics, also in percentages of the respiratory gas, and a lower area of the anesthesia protocol within which the socalled vital parameters are recorded.

The typical content of an anesthesia protocol comprises the following information: the operating area, i.e. the area of the patient's body which has been operated on; the manner in which the patient was positioned during the operation, e.g. laid on his back, laid on his stomach, etc.; the technical means used for the anesthesia, viz. gas monitors as well as measuring instruments for the electrocardiogram, for $CO_2$, for $SO_2$, for the invasive or the non-invasive blood pressure, for the central venous pressure, etc.; the type of artificial respiration or ventilation, viz. the spontaneous respiration (the patient breathes himself), the assisted, viz. machine-assisted respiration, such as IPPV (intermittent positive pressure ventilation), PEEP (the kind of artificial respiration which holds the pressure on a specific level during expiration), etc..

In this lower area of the anesthesia protocol, socalled trend curves, viz. e.g. the trend curves of the systolic and of the diastolic blood pressure as well as the trend curve indicating the cardiac rate, are shown by points above the time axis. When the recording is carried out in the form of point curves, symbols for the various trend curves are typically used, said symbols comprising e.g. triangles, dots and the like.

Some doctors prefer a tabular reproduction of numerical values instead of such reproductions in the form of curves.

Furthermore, in the anesthesia protocols made by hand, socalled events or medically relevant occurrences are recorded in the form of numerical marks at the trend curves, and explanations assigned to these numerical marks are added below the protocol.

If, for example, a sudden rise in the patient's blood pressure occurs, a specific number will be recorded by the side of the blood pressure trend curve at the time the rise in blood pressure occurs, and the medical reasons for this rise in blood pressure are indicated in connection with said number at some other point of the protocol.

Furthermore, for statistical purposes as well as for statements of account, the presence of the anesthetist, the length of the actual time of anesthesia, intubation and extubation are recorded in the anesthesia protocol above the time axis, said data being supplemented by the patient's data and data on persons from the medical sphere who were present.

It is obvious that the manual production of an anesthesia protocol is a substantial additional burden for the anesthetist and that especially during a critical condition of the patient, the precise recording of which would be particularly important in connection with an anesthesia protocol, the anesthetist will normally not find time for updating the anesthesia protocol. Hence, especially in situations which are critical from the medical point of view, the anesthetist will be compelled to make the anesthesia protocol from memory after having the patient protected from acute danger, and this will naturally result in an inaccurate or incomplete anesthesia protocol.

Since these problems have been recognized, automatic anesthesia protocol systems or narcosis protocol systems have already been created, which are connected to patient monitors and to an anesthesia machine via interface connections and which automatically procure the patient's vital parameters from the interfaces in the manner explained hereinbelow, store these parameters and combine them so as to obtain an anesthesia protocol in the manner which will be described hereinafter.

FIG. 1 is a schematic representation of such a known anesthesia protocol system, which has supplied thereto input signals representing at least the socalled vital parameters derived from the patient and supplied to patient monitors MD1, . . . , MDn, the output signals of said monitors being supplied to an interface IF1, IF2. The type of interface is not of decisive importance—neither for the purpose of the present assessment of the prior art nor for the purpose of the present invention. Interfaces which may be used are normal serial interfaces, such as the standard interface RS232, or also special data networks for data of patients, which are offered by the applicant under the name of HP Care-Net-Interface.

The digital curve signals thus produced are stored in a data base by a data processing unit (which is not shown), said data base being organized like a ring buffer having a specific ring buffer length in such a way that, after storage of a number of curve signal values corresponding to the ring buffer length, the respective oldest curve signal value is overwritten by the respective youngest curve signal value. In other words, the data base DB1 has provided therein a plurality of tracks used for storing all the curves and having each a predetermined length, said tracks being repeatedly overwritten with a determinable size like a ring buffer. The data base DB1 has provided therein one "track" for each curve of interest.

In the known system, a monitor MO is provided, which can be controlled by the data processing unit for displaying the real time curves or trend curves.

Furthermore, the known system is capable of automatically producing anesthesia protocols and outputting them either on the monitor or on a printer.

For this purpose, the known system derives from the curves socalled trend curves within the patient monitors. These trend curves are normally values which are derived from the curves and which have a markedly lower time resolution. A trend curve for the systolic and the diastolic blood pressure can, for example, be derived from the curve representing the blood pressure behaviour. Such trend curves are stored in a second data base e.g. with a time resolution of one trend curve signal value per second. The thus obtained point values for the trend curves are then reproduced as a screen display or as a printout of a printer. The curves thus obtained constitute an essential component of the automatically produced anesthesia protocol whose outward appearance largely corresponds to the anesthesia protocol made by hand as far as the representation of the trend curves is concerned.

In the known anesthesia protocol system according to FIG. 1, a screen display or a printout of an anesthesia protocol to be created is produced on the basis of all parameters, which consist of the values stored in the data base DB1 or of the trend curves derived from said values, by selecting one configuration from a predetermined group of configurations. These configurations have been defined in advance in a socalled "off-line" mode in such a way that each segment or field of the anesthesia protocol to be displayed on the screen or to be printed out has assigned thereto a specific parameter. Such a predetermined configuration can, for example, comprise a representation of specific vital parameters and machine parameters of the anesthesia machine in tabular form or in the form of symbols. A different configuration may comprise specific groups of medication parameters in predetermined fields or segments of the anesthesia protocol to be produced, said medication parameters being, for example, the time of administration of medicaments and the time of supply of specific respiratory gases or anesthetic gases. In any case, the configuration of the known anesthesia protocol system for defining a specific screen display or a specific form of printout of the anesthesia protocol is carried out in a single-step mode by directly assigning parameters to the segments of the anesthesia protocol.

In view of the fact that a typical anesthesia protocol comprises a large number of parameters, a modification of the configuration of the known anesthesia protocol system for creating a new display or a new form of printout of an anesthesia protocol entails extensive and troublesome work.

SUMMARY OF THE INVENTION

It is the object of the present invention to provide an anesthesia protocol system configuration method for the screen display of an anesthesia protocol which can be defined by an operator and/or for the form of a printout of an anesthesia protocol which can be defined by an operator, said configuration method simplifying the reconfiguration of the system.

This object is achieved by an anesthesia protocol system configuration method for the screen display of an anesthesia protocol and/or for the form of a printout of an anesthesia protocol, said screen display as well as said form of printout being determinable by an operator, wherein a plurality of parameters comprising a vital parameter of the patient and/or a medication parameter and/or a parameter for an adjustment of gas and/or a parameter of an anesthesia machine are combined in a manner which can be defined by the operator for obtaining the screen display and/or the printout of the anesthesia protocol, said method comprising the following steps:

a) defining a configuration name for each desired configuration;

b) defining all the groups which may be taken into account for a possible future reproduction in a segment of the screen display and/or of the printout of the anesthesia protocol by combining the parameters belonging to the respective group and by assigning a configuration name to this definition;

c) defining a screen display and/or a printout of the anesthesia protocol by assigning a respective one of said groups to each segment of the screen display and/or of the printout of the anesthesia protocol;

d) repeating steps b) and c) for each configuration taken into account and assigning each time a configuration name to each configuration; and e) selecting the desired screen display and/or the desired printout of the anesthesia protocol through the operator by means of the configuration name.

The configuration method according to the present invention uses for the first time a three-step structure for defining the configuration.

By means of a first method step, which should expediently be carried out in an "off-line" mode of the system, all the groups which may be taken into account for a possible future reproduction in a segment of the screen display and/or of the printout of the anesthesia protocol are defined by combining the parameters belonging to the respective groups. Prior to this step or during this step, a configuration name is assigned to this definition.

In a second step, a screen display and/or a printout of the anesthesia protocol is defined by assigning a respective one of said groups to each segment of the screen display and/or of the printout of the anesthesia protocol.

The above-mentioned steps are repeated for each configuration taken into account and a separate configuration name is assiged to each configuration.

In a third step of the method according to the present invention, the operator selects the desired screen display and/or the desired form of printout of the anesthesia protocol by means of the configuration name, said third step being carried out in an "on-line" mode, i.e. during the production of the anesthesia protocol.

The three-step structuring of the configuration of the anesthesia protocol system according to the present invention permits a simple, fast and flexible production of various anesthesia protocols satisfying the personal demands or ideas of the anesthetist who works with the system in question.

In a preferred embodiment of the invention, the steps a), b) and c) are carried out in a so-called off-line mode outside a program for generating and displaying on a screen and/or printing out the anesthesia protocol.

In another preferred embodiment of the method in accordance with the invention, the step d) is carried out in a socalled on-line mode during the program used for generating and displaying on a screen and/or printing out the anesthesia protocol.

In another preferred embodiment of the method in accordance with the invention, prior to step a), a parameter pool is formed in such a way that, among the vital parameters supplied by patient monitors (MD1, . . . , MDn), those parameters are eliminated which are redundant or which correspond to one another so that the parameter pool will include each vital parameter only once;

wherein, prior to step a), a medication pool is additionally formed on the basis of medication parameters indicating the nature and the amount of the gases and/or anesthetics and/or medicaments and/or infusions and/or transfusions supplied to the patient; and wherein step b), in which the groups are defined, combines the vital parameters and/or the medication parameters so as to form groups.

Further developments of the configuration method according to the present invention are defined in the subclaims.

SHORT DESCRIPTION OF THE DRAWINGS

In the following, preferred examples of the method according to the present invention will be explained in detail with reference to the drawings enclosed, in which.

DESCRIPTION OF THE PREFERRED EMBODIMENTS OF THE INVENTION

Figure 1:
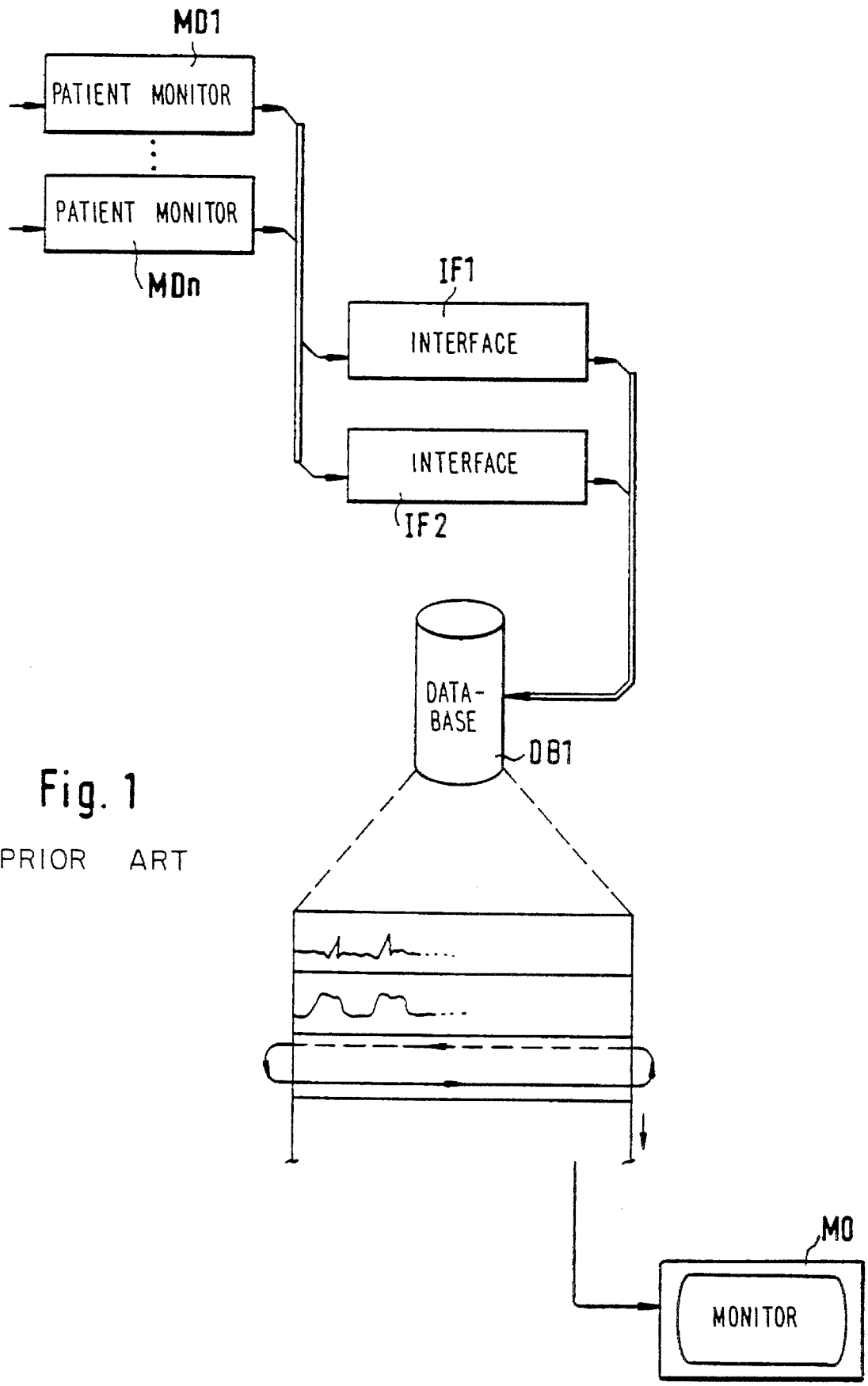
FIG. 1 is a block diagram of a known anesthesia protocol system.
Figure 2A:
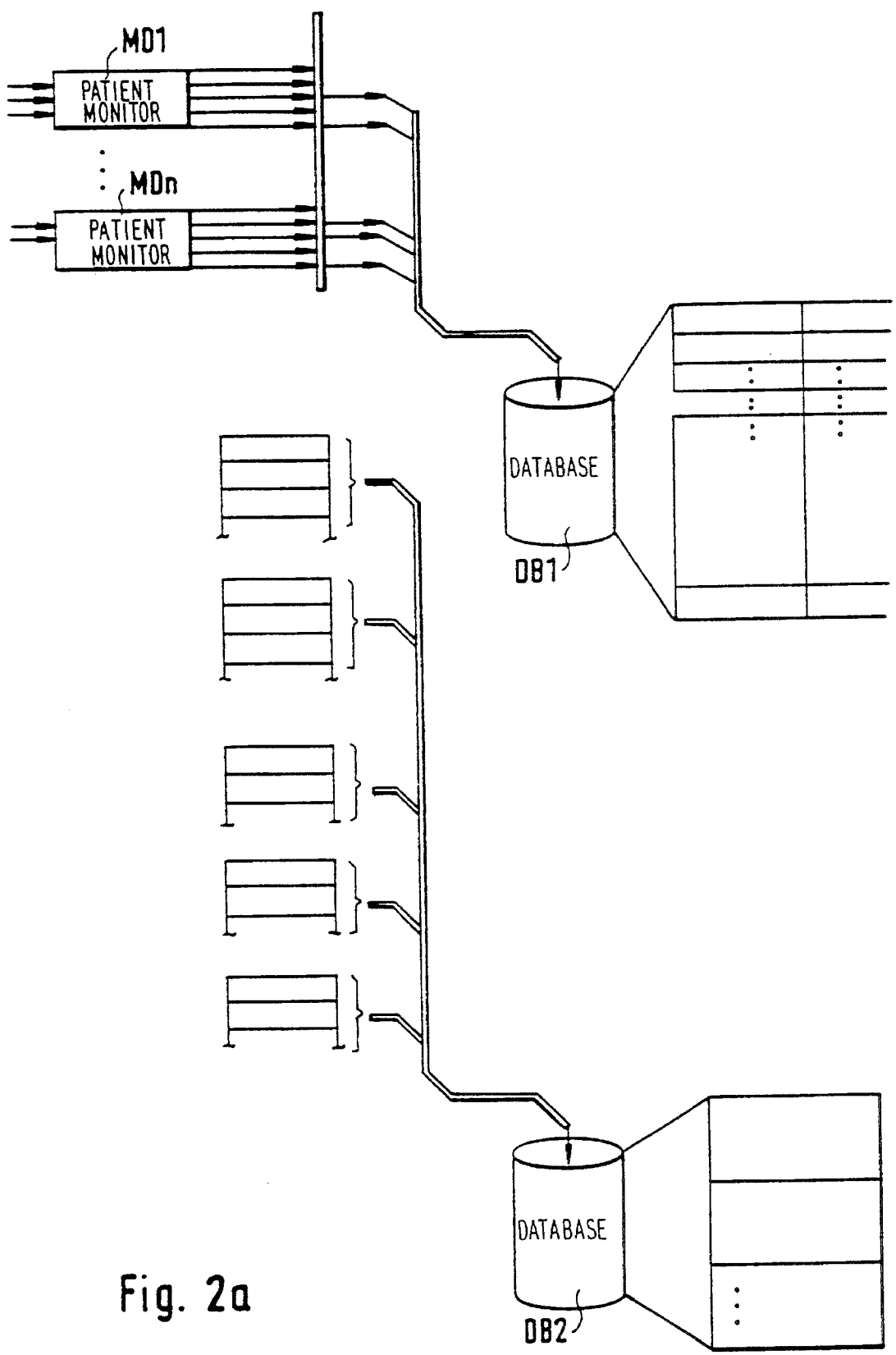
FIGS. 2a, 2b and 2c are block diagrams for elucidating the anesthesia protocol system configuration method according to the present invention.
Figure 2B:
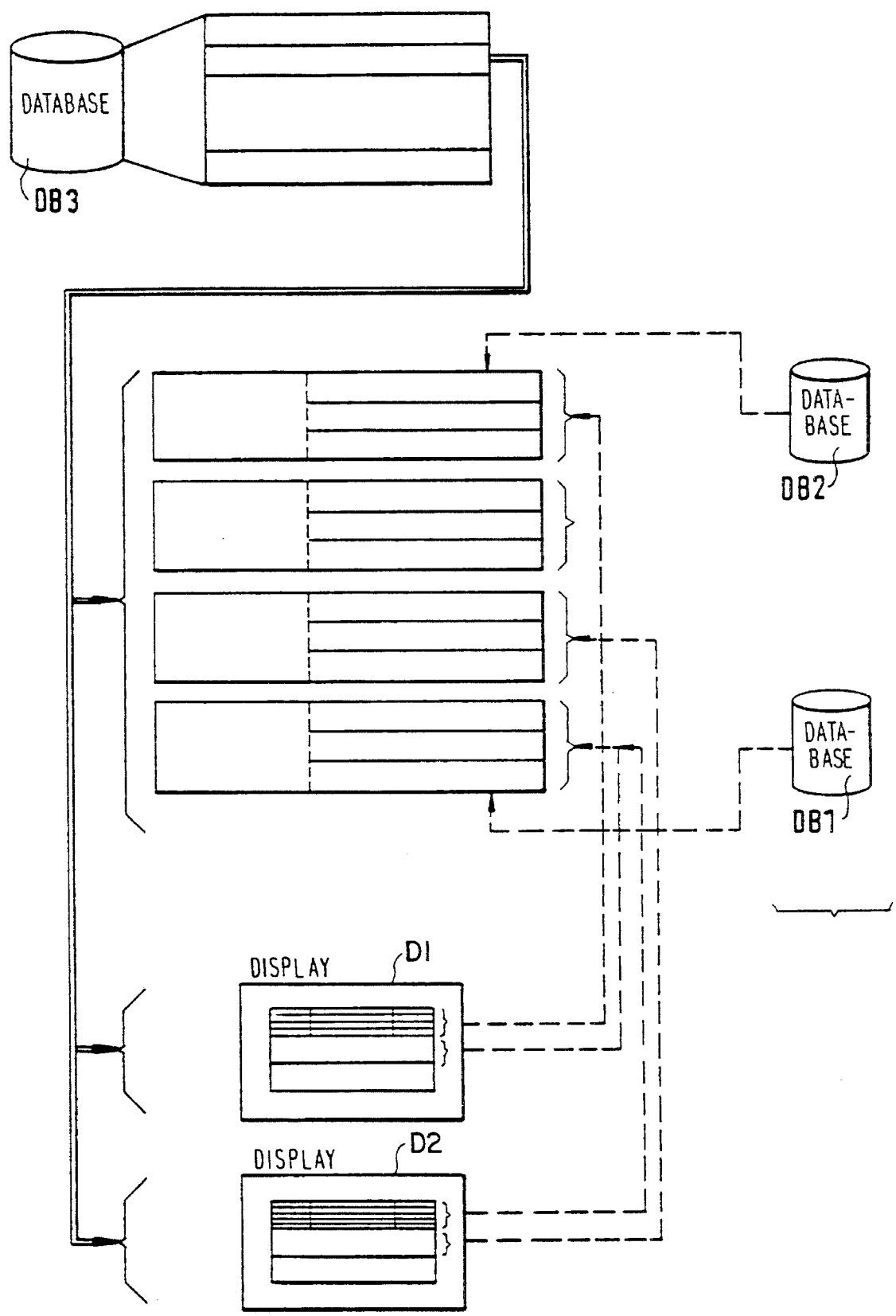
Figure 2C:
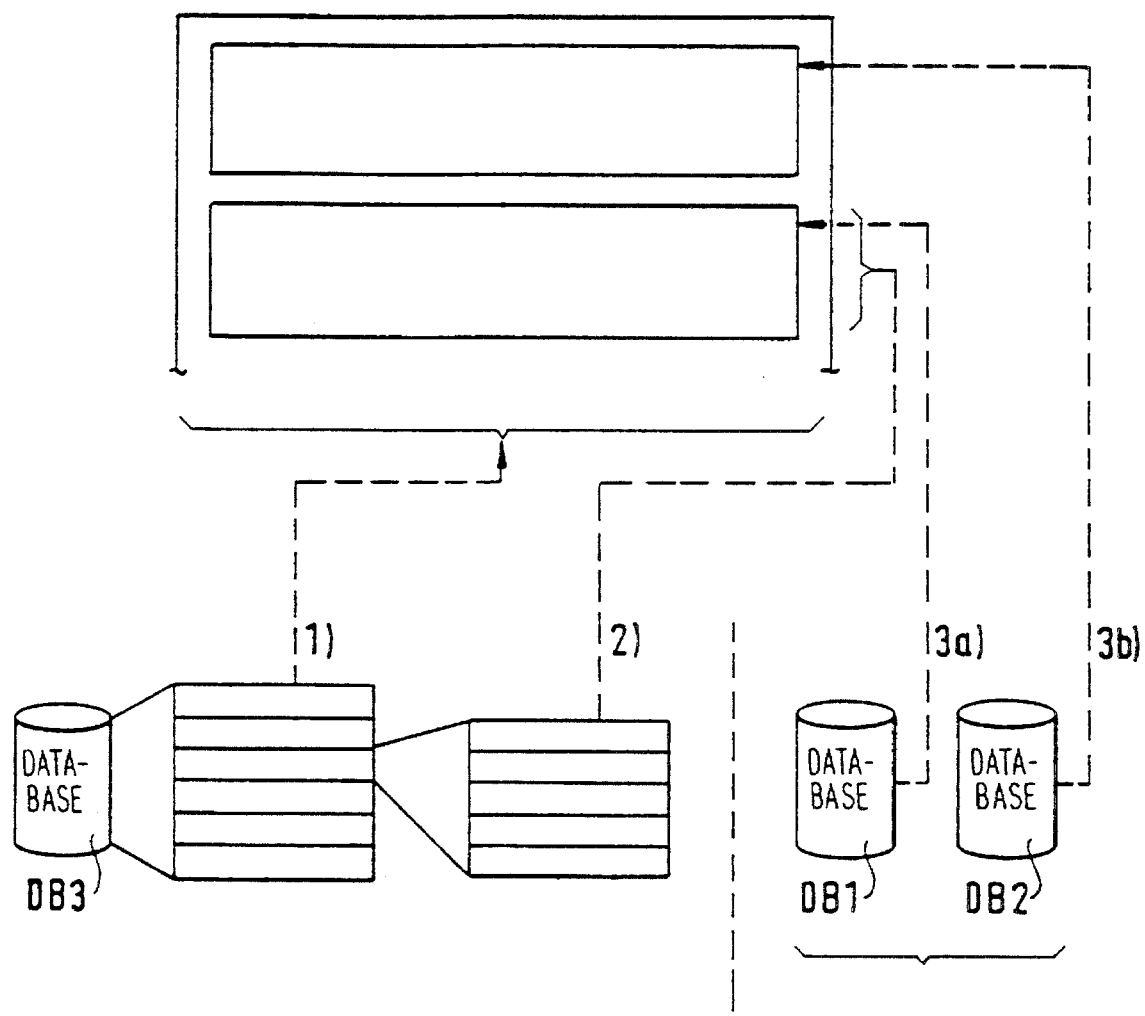

A plurality of vital parameters, which are detected by means of patient monitors MD1, . . . , MDn FIG. 2a, are supplied via system interfaces IF of the type used in the prior art and illustrated in FIG. 1 to the anesthesia protocol system in a manner which is known per se, said anesthesia protocol system combining these vital parameters in a first data base DB1 FIGS. 2a, 2b and 2c, in the form of a so-called parameter pool. In this first step, parameters of interest, which may, for example, be the cardiac rate, the systolic or diastolic blood pressure, etc., are selected. A selection is necesssary, since various medical devices, which form the patient monitors MD1, . . . , MDn, supply partly identical or redundant parameters among which only the parameters which are relevant with regard to future anesthesia protocol formation are chosen.

After this selection, the list of parameters produced in the first data base DB1 includes each parameter only once, i.e. the cardiac rate, for example, is included only once notwithstanding the fact that various patient monitors each supply information on the cardiac rate independently. The parameter pool thus formed is device-independent and includes each parameter only once.

Parallel to said parameter pool, a medication pool is formed whose parameters comprise information on the amount of respiratory gas, the kind of anesthetic gas and the amount of anesthetic gas, kinds and amounts of infusions and transfusions and the like. This medication pool is filed in a second data base DB2 in FIGS. 2a, 2b, and 2c, which may correspond to the first data base DB1 with regard to its structure.

The sequence of method steps following hereinafter is carried out once for each configuration. Taking as a basis the parameters contained in the parameter pool and in the medication pool, all the groups which may possibly be reproduced later on in a segment of a screen display or of a printout of the anesthesia protocol to be produced are defined in the next step by combining the respective parameters belonging to one group. When this step is being started, a configuration name is assigned. When a plurality of parameters is combined in this way so as to form one group in each case, a pool of groups assigned to the configuration in question will be obtained. The pool of groups represents those combinations of parameters variable above the time axis which are to be displayable in combination, said parameters being, for example, medicaments, infusions, transfusions and vital parameters.

Each anesthesia protocol to be produced includes plural segments. In the example shown, each anesthesia protocol comprises three segments.

In the second main step of the configuration method according to the present invention, a plurality of possible screen displays D1 and D2, FIG. 2b, and/or forms of printout of the anesthesia protocol is defined by assigning to each segment of each screen display and/or form of printout of the anesthesia protocol one of the groups of said pool of groups. Also this assigning is carried out in an off-line mode, i.e. prior to the actual use of the anesthesia protocol system for producing the anesthetic protocols. The two-step method which has been described up to now is carried out once for each configuration which may possibly be reproduced, and whenever said two-step method is carried out different configuration names are assigned to the various configurations.

After this off-line configuration of the system, a configuration of the system can be effected by the operator in a third method step within the on-line mode, i.e. during the actual production of the anesthesia protocol by the anesthesia protocol system, by selecting the desired screen display D1, D2 and/or the desired printout of the anesthesia protocol by means of the configuration name.

On the basis of the above description, it will be obvious to the person skilled in the art that anesthetic protocol systems of the type described may detect a number of data wich is substantially larger than the number of data which can be displayed on a single display for an anesthesia protocol. The measures of assigning first specific parameters to specific groups and, subsequently, specific groups to segments of a display in an off-line mode permits a simple off-line preconfiguration of the system, and this off-line preconfiguration can be extended by additional configurations with little effort. It is, for example, possible to select from a pool of groups a fully configured display segment with a preselected group of parameters so that parameters of this type belonging together for medical reasons can be made a segment of the anesthesia protocol by means of a single selecting operation.

One example of a group formation carried out during the generation of the pool of groups is, for example, the combination of the anesthesia machine parameters or the combination of specific vital parameters of the patient. The off-line pregrouping performed by creating the pool of groups will make it easier for the user to create new types of anesthetic protocols by compiling suitable groups.

The configuration name, which has already been assigned upon starting the step in which the pool of groups is created, may, for example, be the name of the anesthetist in charge or the designation of the anesthesia to be carried out or of the medical procedure to be performed.

This means that each of the screen displays D1, D2 which will be selectable in the on-line mode later on has assigned thereto a configuration name by means of which the appropriate screen display can be called.

Deviating from the method described, it is also possible to take as a basis the groups which have been formed by producing the pool of groups and to carry out an on-line compilation of the screen display by making use of the predefined groups. Also when this alternative is used, it is possible to incorporate, by direct selection, a missing parameter into the screen display D1, D2 or into the printout during the on-line mode, i.e. the mode of operation in which the anesthesia protocol is produced by means of the screen or the printer, for modifying thus a previous group definition in such a way that a missing parameter can additionally be included. Such a modification of the predefined group preferably has only a temporary effect and influences solely the current screen display.

We claim:

1. An anesthesia protocol system configuration method of displaying on a screen an anesthesia protocol image and/or printout form of an anesthesia protocol, the screen display as well as the printout form being determinable by an operator, the method resulting in plural parameters including a vital patient parameter and/or a medication parameter and/or a parameter for adjusting anesthesia gas and/or a parameter of an anesthesia machine being combined in a manner which can be defined by the operator so the screen display and/or the printout of the anesthesia protocol is obtained, the method comprising:

a) selecting a configuration name for each desired configuration;
   b) selecting one or more parameters from said plural parameters and combining the selected parameters to form one or more groups containing the parameters of interest;
   c) assigning selected ones of the formed groups to predefined segments on the screen display and/or the printout to define the screen display and/or the printout of the anesthesia protocol;
   d) repeating steps b) and c) for each configuration taken into account, and each time selecting a configuration name for each configuration; and
   e) selecting the desired screen display and/or the desired printout of the anesthesia protocol by the operator using the configuration name.

2. A method according to claim 1 wherein steps a), b) and c) are carried out in a so-called off-line mode outside a program for generating and displaying on a screen and/or printing out the anesthesia protocol.

3. A method according to claim 1 wherein step d) is carried out in a so-called on-line mode during a program used for generating and displaying on a screen and/or printing out the anesthesia protocol.

4. A method according to claim 1 wherein, prior to step a), a parameter pool is formed in such a way that, among the vital parameters supplied by patient monitors, those parameters are eliminated which are redundant or which correspond to one another so that the parameter pool includes each vital parameter only once;

wherein, prior to step a), a medication pool is additionally formed on the basis of medication parameters indicating the nature and the amount of the anesthesia gases and/or anesthetics and/or medicaments and/or infusions and/or transfusions supplied to the patient; and combining the vital parameters and/or the medication parameters to form the groups during step b), during which the groups are formed.

5. A method according to claim 1 wherein, prior to step a), a parameter pool is formed in such a way that, among the vital parameters supplied by patient monitors, those parameters are eliminated which are redundant or which correspond to one another so that the parameter pool includes each vital parameter only once.

6. A method according to claim 1 wherein, prior to step a), a parameter pool is formed in such a way that, among the vital parameters supplied by patient monitors, those parameters are eliminated which are redundant or which correspond to one another so that the parameter pool includes each vital parameter only once;

wherein, prior to step a), a medication pool is additionally formed on the basis of medication parameters indicating the nature and the amount of the anesthesia gases and/or anesthetics and/or medicaments and/or infusions and/or transfusions supplied to the patient.

7. A method according to claim 1 wherein, prior to step a), parameter pool is formed in such a way that, among the vital parameters supplied by patient monitors, those parameters are eliminated which are redundant or which correspond to one another so that the parameter pool includes each vital parameter only once; and combining the vital parameters and/or the medication parameters to form the groups during step b), during which the groups are formed.

* * * * *